US 6,573,401 B1

(12) United States Patent
Bosch i Lladó et al.

(10) Patent No.: US 6,573,401 B1
(45) Date of Patent: Jun. 3, 2003

(54) PROCESS FOR PRODUCING 4-AMINO-1-HYDROXYBUTYLIDENE-1,1-BISPHOSPHONIC ACID AND ITS TRIHYDRATED MONOSODIUM SALT

(75) Inventors: Jordi Bosch i Lladó, Girona (ES); Eugenia Pagans Lista, Celrà (ES); Ma del Carmen Onrubia Miguel, Barcelona (ES)

(73) Assignee: Medichem, S.A., Barcelona (ES)

( * ) Notice: Subject to any disclaimer, the term of this patent is extended or adjusted under 35 U.S.C. 154(b) by 0 days.

(21) Appl. No.: 10/048,267

(22) PCT Filed: Jul. 17, 2000

(86) PCT No.: PCT/ES00/00254

§ 371 (c)(1),
(2), (4) Date: Jan. 28, 2002

(87) PCT Pub. No.: WO01/10874

PCT Pub. Date: Feb. 15, 2001

(30) Foreign Application Priority Data

Aug. 6, 1999 (ES) .............................. 9901806

(51) Int. Cl.$^7$ ................................. C07F 9/38
(52) U.S. Cl. ...................................... 562/13
(58) Field of Search ..................... 562/9, 11, 12, 562/13

(56) References Cited

U.S. PATENT DOCUMENTS

| | | | |
|---|---|---|---|
| 4,407,761 A | 10/1983 | Blum et al. | |
| 4,624,947 A * | 11/1986 | Blum et al. | 514/108 |
| 4,705,651 A | 11/1987 | Staibano | |
| 4,711,880 A * | 12/1987 | Stahl et al. | 514/103 |
| 4,922,007 A | 5/1990 | Kieczykowski et al. | |
| 5,019,651 A | 5/1991 | Kieczykowski | |
| 5,039,819 A | 8/1991 | Kieczykowski | |
| 5,648,491 A | 7/1997 | Dauer et al. | |
| 5,908,959 A * | 6/1999 | Kubela et al. | 562/13 |
| 6,201,148 B1 * | 3/2001 | Lidor-Hadas et al. | 562/13 |

FOREIGN PATENT DOCUMENTS

| | | |
|---|---|---|
| EP | 0 462 663 B1 | 12/1991 |
| EP | 0 462 663 A1 | 12/1991 |
| EP | 0 494 844 A1 | 7/1992 |
| GB | 2 248 061 A | 3/1992 |
| WO | WO 95/06052 | 3/1995 |
| WO | WO 98/34940 | 8/1998 |

* cited by examiner

Primary Examiner—Jean F. Vollano
(74) Attorney, Agent, or Firm—Scully, Scott, Murphy & Presser

(57) ABSTRACT

The invention relates to a process for the preparation of 4-amino-1-hydroxybutylidene-1,1-bisphosphonic acid and of the trihydrated monosodium salt thereof, consisting of reacting 4-aminobutyric acid with a phosphonation mixture formed by phosphorous acid and methanesulfonic anhydride and thereafter hydrolyzing the product of said reaction and isolating the products by adjustment of the pH.

13 Claims, No Drawings

PROCESS FOR PRODUCING 4-AMINO-1-HYDROXYBUTYLIDENE-1,1-BISPHOSPHONIC ACID AND ITS TRIHYDRATED MONOSODIUM SALT

This application is a 371 of PCT/ES00/00254 filed Jul. 17, 2000, now WO 01/0874

FIELD OF THE INVENTION

This invention relates to an improved process for the preparation of 4-amino-1-hydroxybutylidene-1,1-bisphosphonic acid and of the trihydrated monosodium salt thereof, respectively known by the International Nonproprietary Names (INN) thereof as alendronic acid and sodium alendronate, and which are useful for the treatment and prevention of diseases involving bone resorption, such as malign hypercalcemia, Paget's disease, osteoporosis, etc.

PRIOR ART REFERENCE

U.S. Pat. No. 4,407,761 describes the preparation of 4-amino-1-hydroxybutylidene-1,1-bisphosphonic acid, by treating 4-aminobutyric acid (GABA) with a phosphonation reactant, followed by hydrolysis of the reaction mixture by the addition of concentrated hydrochloric acid and subsequent heating of said mixture. The said patent describes the use of three phosphonation mixtures: $H_3PO_3/PCl_3$, $H_3PO_3/PCl_5$ and $H_3PO_3/POCl_3$.

U.S. Pat. No. 4,705,651 is bound to the use of a phosphonation mixture consisting of a mixture of $H_3PO_3/PCl_3$ and to a certain $GABA/H_3PO_3/PCl_3$ stoichiometry.

It is hard to adapt these processes to industrial production, since the reaction mixture of the phosphonation step is not homogenous and tends to solidify, preventing stirring, and also the yields obtained are variable. Under these conditions, the subsequent hydrolysis step entails substantial risk, due to the presence of small drops of $PCl_3$ occluded in the reaction mixture and which may cause local overheating on contact with the hydrolyzing agent and also explosion of the gases generated.

U.S. Pat. No. 4,922,007 describes the use of methanesulfonic acid to avoid the lack of homogeneity and the solidification of the reaction mixture during the phosphonation step, to which end the ternary system $H_3PO_3/PCl_3/CH_3SO_3H$ is proposed. This system has been developed in other later patents as far as complementary aspects are concerned. Among such patents there may be cited EP-A-0 462 663 and U.S. Pat. No. 5,019,651, on the control of pH in the hydrolysis phase, and EP-A-0 715 631 and U.S. Pat. No. 5,648,491, concerning a continuous process.

The present inventors are unaware of other descriptions of direct phosphonation of 4-aminobutyric acid proposing phosphonation reactants other than the above mentioned mixtures.

U.S. Pat. No. 5,039,819 describes an method of indirect phosphonation of 4-aminobutyric acid requiring the protection of the amino group with phthalic anhydride, activation of the acid with thionyl chloride, reaction with an alkyl phosphite and, finally, final hydrolysis of the phosphonic esters obtained, a time-consuming process which is inappropriate for industrial purposes.

There is, therefore, a need to develop alternative processes for the preparation of 4-amino-1-hydroxybutylidene-1,1-bisphosphonic acid and salts thereof, allowing the industrial preparation of these products to be simplified.

OBJECT OF THE INVENTION

The object of the present invention is a new process for the preparation of 4-amino-1-hydroxybutylidene-1,1-bisphosphonic acid and of the trihydrated monosodium salt thereof, which is easily adapted to industrial application, with good yields, which does not require the use of reactants such as $PCl_3$, $PCl_5$ or $POCl_3$, which are highly toxic and hazardous products for the environment, and in which the reaction mixture does not solidify.

DESCRIPTION OF THE INVENTION

The present inventors have discovered that a mixture of phosphorous acid and methanesulfonic anhydride allows the direct bisphosphonation of 4-aminobutyric acid to give the corresponding 4-amino-1-hydroxybutylidene-1,1-bisphosphonic acid with good results and without the reaction mixture solidifying.

Consequently, the process according to the invention consists of reacting 4-aminobutyric acid with a phosphonation mixture and hydrolyzing the resulting reaction product to subsequently isolate, by an appropriate pH adjustment, the free acid or the monosodium salt. The essential feature of this process is that the phosphonation mixture is formed by phosphorous acid and methanesulfonic anhydride.

Although this phosphonation mixture may also be used jointly with other auxiliary phosphonation reactants, such as $PCl_3$, $PCl_5$ or $POCl_3$, in a specially preferred form the phosphonation mixture is formed exclusively by phosphorous acid and methanesulfonic anhydride.

In the said phosphonation mixture, the phosphorous acid/methanesulfonic anhydride molar ratio may range from 2:5 to 5:2, although a phosphorous acid/methanesulfonic anhydride molar ratio of 1:1 is preferred.

With regard to the 4-aminobutyric acid/phosphorous acid molar ratio, the latter being the reactant providing the two phosphonic groups to the structure of the end products, it may range from 2:1 to 5:1, 3:1 being preferred.

A preferred embodiment of the process according to the invention comprises the following steps:

(i) reacting 4-aminobutyric acid with phosphorous acid in the presence of methanesulfonic anhydride, (ii) hydrolyzing the reaction mixture with water, (iii) adjusting the pH of the hydrolyzed mixture to 4.3 with the addition of a solution of sodium hydroxide or of a basic sodium salt, (iv) precipitating the trihydrated monosodium salt by cooling and recovering the product obtained by filtration and drying, and if it is desired to obtain the free acid, (v) converting the salt obtained into the corresponding acid by neutralization thereof with an acid stronger than the 4-amino-1-hydroxybutilidene-1,1-bisphosphonic acid.

The most appropriate temperatures for the bisphosphonation reaction range from 45° C. to 125° C., preferably from 65° C. to 75° C.

Although it is not necessary, the bisphosphonation reaction is preferably conducted in the presence of inert organic solvents which do not solubilize the reaction product. An inert solvent is understood to be one which, in the opinion of the man or the art, does not react substantially with the reactants involved. Preferred among the inert solvents are the aromatic hydrocarbons such as xylene, toluene, benzene, etc.

Once the bisphosphonation reaction is complete, it is interrupted by the addition of water at a temperature ranging from 0° C. to 90° C., preferably 0° C. to 40° C. The resulting mixture is heated to a temperature above 50° C., preferably to the reflux temperature of said mixture, to ensure complete hydrolysis. The amount of water added for the hydrolysis is, preferably, equal to or more than 6.5 mL per gram of 4-aminobutyric acid.

Preferably, prior to isolating the sodium salt by filtration, a treatment step with activated carbon is included, at a temperature below the boiling point of water, so as to remove remains of sulfur compounds. Alternatively, this treatment may be carried out at room temperature, on completion of the hydrolysis step.

If desired, once the sodium salt has been obtained, the 4-amino-1-hydroxybutylidene-1,1-bisphosphonic acid may be obtained by neutralization of a solution of the salt with an acid stronger than the 4-amino-1-hydroxybutylidene-1,1-bisphosphonic acid itself, for example, hydrochloric acid, sulfuric acid, etc., in a way clearly within the reach of a man of the art.

Another way of obtaining the 4-amino-1-hydroxybutylidene-1,1-bisphosphonic acid consists of omitting the neutralization step on completion of the hydrolysis and precipitating the acid directly.

The process according to the invention is simple and economic, since it only requires simple industrial operations, the yields obtained are good and the necessary starting raw materials may be acquired on the marketplace.

The most important advantages of the process according to the invention consists of: 1) avoiding the use of $PCl_3$, $PCl_5$ or $POCl_3$ as dehydrating agents in the phosphonation reaction, which obviates the handling of these reactants which are highly toxic and hazardous, as well as the release of HCl during the reaction; and 2) the fact that the presence of methanesulfonic anhydride keeps the reaction mixture fluid, without the occurrence of solidification, which makes stirring difficult.

The following examples are given for the purpose of providing the man of the art with a sufficiently clear and complete explanation of the present invention, but must not be considered as limitations on the essential aspects of the object thereof, as set forth in the foregoing paragraphs of this description.

EXAMPLES

Example 1

12.53 g (0.122 mole) of γ-aminobutyric acid, 29.83 g (0.364 mole) of phosphorous acid and 63.35 g (0.364 mole) of methanesulfonic anhydride were charged into a 500 mL balloon flask equipped with mechanical stirring, thermometer, cooling, nitrogen pressurization and gas adsorption traps. The thus obtained solid mixture was heated over 1 h 45 min to 70° C. and was held at this temperature for 3 hours. At the end of this time, the temperature of the mixture was raised to 100° C., and was held at this temperature for a further 3 hours. Thereafter it was allowed to cool to room temperature and then 80.8 mL of deionized water were added over 15 min, with the temperature being held to between 30–40° C. The thus obtained mixture was held at reflux for 6 hours (approximate temperature: 100° C.), was allowed to cool and the pH was adjusted to 4.3 by the addition of approximately 84 mL of a 40% sodium hydroxide solution. The suspension obtained was filtered, the solid was washed twice over the filter with 10 mL of cold water and 49.88 g of moist crude product were obtained.

47.86 g of this crude product were dissolved in 24 mL of water under reflux, the solution obtained was cooled to 0–5° C. over 40 min, and was held at this temperature for approximately 21 h 30 min, after which is was filtered and the solid was washed twice over the filter with 5 mL of cold water. 35.39 g of moist product were obtained, of which 32.81 g were redissolved in 42 mL of water under reflux. The solution obtained was cooled to 0–5° C. over 40 min, with precipitation of the product being observed at 74° C. It was held at this temperature for approximately 16 hours and was then filtered, the solid being washed twice over the filter with 5 mL of cold water. 30.05 g of moist product were obtained and were dried at 40° C. under vacuum until a constant weight was obtained, to give 27.24 g of sodium alendronate (trihydrated monosodium salt of 4-amino-1-hydroxybutylidene-1,1-bisphosphonic acid). Overall yield: 77.7%.

Example 2

5.92 g (0.057 mole) of γ-aminobutyric acid, 14.13 g (0.173 mole) of phosphorous acid and 30.05 g (0.173 mole) of methanesulfonic anhydride were charged into a 500 mL balloon flask equipped with mechanical stirring, cooling, thermometer and nitrogen pressurization. The thus obtained mixture of solids was heated to 70° C. over 1 h 40 min and was held at this temperature for 9 hours. At the end of this time, the reaction mixture was allowed to cool to room temperature and then 38.6 mL of deionized water were added, with the temperature being held to below 40° C. throughout the addition. Thereafter, the mixture was held at reflux for 6 hours (approximate temperature: 110° C.), was allowed to cool and the pH was adjusted to 4.3 by the addition of approximately 49 mL of a 40% sodium hydroxide solution.

The suspension obtained was dissolved at 70° C. by the addition of 200 mL of water, 0.94 g of activated carbon were charged, the mixture was held under stirring for 30 min at 70–76° C. and was then filtered through a pre-layer of Avicel in hot water, the pre-layer being washed three times with 10 mL of hot water. The 200 ml of added water were removed by distillation at reduced pressure and the thus obtained suspension was cooled to 0–5° C., was held for 3 hours at this temperature and was then filtered, the solid being washed twice over the filter with 10 mL of cold water. 14.06 g of moist product were obtained and when dried at 40° C. under vacuum to a constant weight gave 12.94 g of sodium alendronate trihydrate. Overall yield: 69.3%.

Example 3

29.68 g (0.288 mole) of γ-aminobutyric acid, 70.69 g (0.862 mole) of phosphorous acid, 150.27 g (0.862 mole) of methanesulfonic anhydride and 350 mL of toluene were charged into a 500 mL balloon flask equipped with mechanical stirring, cooling, thermometer and nitrogen pressurization. The thus obtained suspension was heated to 70° C. over 1 h 40 min and was held at this temperature for 9 h 30 min. The reaction mixture was then allowed to cool and 193 mL of deionized water were added over 45 min, with the temperature being held to below 40° C. The mixture was held under stirring for 30 min at room temperature and thereafter the phases were separated. The aqueous upper phase was heated and when reflux was reached, a volume of 48 mL of water was distilled off to entrain the residual toluene. The volume of water removed by distillation was replaced and the mixture was held under reflux for a total of 6 hours (approximate reflux temperature: 115° C.). The thus obtained solution was adjusted to pH 4.3 by the addition of 162 mL of a 40% sodium hydroxide solution.

The suspension obtained was dissolved at 70° C. by the addition of 1 L of deionized water and 4.67 g of activated carbon were charged. The mixture was held under stirring for 30 min at 70° C., was cooled to 55° C. and was filtered at this temperature through a pre-layer of Avicel in hot water, the pre-layer being washed three times with 50 mL of hot water. The thus obtained solution was distilled at reduced pressure to remove the volume of water (1 L) added in the previous step and the thus obtained suspension was cooled to 0–5° C. and held at this temperature for 3 hours. The suspension was then filtered, the solid being washed twice over the filter with 20 mL of cold water and 73.81 g of moist crude product were obtained.

23.01 g of this moist crude product were dissolved in 28.3 mL of deionized water under reflux, the thus obtained solution was cooled to 0–5° C. It was filtered, with the solid being washed twice over the filter with 5 mL of cold water and 21.21 g of moist product were obtained which, when dried at 40° C. under vacuum to constant weight, gave 19.19 g of sodium alendronate trihydrate. Overall yield: 65.6%.

What is claimed is:

1. A process for the preparation of 4-amino-1-hydroxybutylidene-1,1-bisphosphonic acid and of the trihydrated monosodium salt thereof consisting of reacting 4-aminobutyric acid with a phosphonation mixture and hydrolyzing the resulting reaction product to subsequently isolate, by an appropriate pH adjustment, the free acid or the monosodium salt, wherein the phosphonation mixture is formed by phosphorous acid and methanesulfonic anhydride.

2. The process of claim 1, wherein the phosphonation mixture is formed exclusively by phosphorous acid and methanesulfonic anhydride.

3. The process of claim 1 or claim 2, wherein the phosphorous acid/methanesulfonic anhydride molar ratio in the phosphonation mixture ranges from 2:5 to 5:2.

4. The process of claim 3, wherein the phosphorous acid/methanesulfonic anhydride molar ratio is 1:1.

5. The process of claim 1, wherein the phosphorous acid/4-aminobutyric acid molar ratio ranges from 2:1 to 5:1.

6. The process of claim 1, comprising the following steps:
   (i) reacting 4-aminobutyric acid with phosphorous acid in the presence of methanesulfonic anhydride,
   (ii) hydrolyzing the reaction mixture with water,
   (iii) adjusting the pH of the hydrolyzed mixture to 4.3 with the addition of a solution of sodium hydroxide or of a basic sodium salt,
   (iv) precipitating the trihydrated monosodium salt by cooling and recovering the product obtained by filtration and drying, and if it is desired to obtain the free acid,
   (v) converting the salt obtained into the corresponding acid by neutralization thereof with an acid stronger than the 4-amino-1-hydroxybutilidene-1,1-bisphosphonic acid.

7. The process of claim 6, wherein step (i) is conducted at a temperature ranging from 65° C. to 75° C.

8. The process of claim 6 or claim 7, wherein step (i) is conducted in the presence of an inert organic solvent.

9. The process of claim 8, wherein the inert organic solvent is an aromatic hydrocarbon.

10. The process of claim 6, wherein the phosphorous acid/methanesulfonic anhydride/4-aminobutyric acid molar ratio is 3:3:1.

11. The process of claim 6, wherein in the hydrolysis of step (ii) an amount of water equal to or more than 6.5 mL is used for each gram of 4-aminobutyric acid used.

12. The process of claim 6, wherein the solution obtained in step (ii) is heated to reflux prior to proceeding to step (iii).

13. The process of claim 6, wherein step (iii) is conducted at a temperature ranging from 15° C. to 25° C.

* * * * *